United States Patent
Chandran et al.

(10) Patent No.: US 7,593,778 B2
(45) Date of Patent: Sep. 22, 2009

(54) ELECTROSURGICAL DEVICE WITH IMPROVED VISIBILITY

(75) Inventors: Subashini Chandran, Toronto (CA); Krishan Shah, Mississauga (CA)

(73) Assignee: Baylis Medical Company Inc., Montreal (CA)

( * ) Notice: Subject to any disclaimer, the term of this patent is extended or adjusted under 35 U.S.C. 154(b) by 0 days.

(21) Appl. No.: 11/079,318

(22) Filed: Mar. 15, 2005

(65) Prior Publication Data

US 2005/0159797 A1 Jul. 21, 2005

Related U.S. Application Data

(63) Continuation-in-part of application No. 10/382,836, filed on Mar. 7, 2003.

(51) Int. Cl.
*A61N 1/04* (2006.01)
*A61N 1/34* (2006.01)

(52) U.S. Cl. ......................... 607/116; 607/46
(58) Field of Classification Search ................ 128/898; 607/96–117
See application file for complete search history.

(56) References Cited

U.S. PATENT DOCUMENTS

| | | | |
|---|---|---|---|
| 4,041,931 A | 8/1977 | Elliott et al. | |
| 4,202,349 A | 5/1980 | Jones | |
| 4,257,429 A | 3/1981 | Dickhudt et al. | |
| 4,419,095 A * | 12/1983 | Nebergall et al. | 604/103.1 |
| 4,447,239 A | 5/1984 | Krutten | |
| 4,657,024 A | 4/1987 | Coneys | |
| 5,209,749 A | 5/1993 | Buelna | |
| 5,383,924 A * | 1/1995 | Brehier | 607/126 |
| 5,415,664 A * | 5/1995 | Pinchuk | 623/1.11 |
| 5,429,597 A | 7/1995 | DeMello et al. | |
| 5,429,617 A * | 7/1995 | Hammersmark et al. | 604/264 |
| 5,433,739 A * | 7/1995 | Sluijter et al. | 607/99 |

(Continued)

FOREIGN PATENT DOCUMENTS

CA 1160932 1/1984

(Continued)

OTHER PUBLICATIONS

Bogduk N, MacIntosh J, Marsland A. "Technical Limitations to the Efficacy of Radiofrequency Neurotomy for Spinal Pain". Neurosurgery 20(4):529-535, 1987.

(Continued)

*Primary Examiner*—Carl H Layno
*Assistant Examiner*—Brian T Gedeon
(74) *Attorney, Agent, or Firm*—Dimock Stratton LLP (57) ABSTRACT

A method and apparatus are disclosed for improving accuracy of placement of a cannula during delivery of electrical energy proximate to bodily tissue, e.g. neural structures. The apparatus optionally includes a cannula operable to deliver electrical current where a portion of the cannula is electrically insulated and a portion of the cannula is exposed and electrically conductive. The cannula further includes a radiopaque marker to identify a specific portion of the cannula, for example to differentiate the electrically insulated region from the electrically exposed region, by allowing it to be more clearly delineated using fluoroscopy or other radiographic imaging techniques. The radiopaque marker is optionally tapered in order to reduce the force required to insert a cannula comprising a radiopaque marker into the patient's body.

18 Claims, 6 Drawing Sheets

U.S. PATENT DOCUMENTS

| | | | |
|---|---|---|---|
| 5,571,147 A | 11/1996 | Sluijter et al. | |
| 5,693,043 A | 12/1997 | Kittrell et al. | |
| 5,759,174 A | 6/1998 | Fischell et al. | |
| 5,779,642 A | 7/1998 | Nightengale | |
| 5,800,428 A | 9/1998 | Nelson et al. | |
| 5,855,577 A | 1/1999 | Murphy-Chutorian et al. | |
| 5,885,227 A * | 3/1999 | Finlayson | 600/585 |
| 6,056,743 A | 5/2000 | Ellis et al. | |
| 6,126,654 A | 10/2000 | Giba et al. | |
| 6,146,380 A | 11/2000 | Racz et al. | |
| 6,190,380 B1 * | 2/2001 | Abela | 606/28 |
| 6,235,000 B1 * | 5/2001 | Milo et al. | 604/164.01 |
| 6,251,104 B1 | 6/2001 | Kesten et al. | |
| 6,306,132 B1 | 10/2001 | Moorman et al. | |
| 6,315,790 B1 | 11/2001 | Gerberding et al. | |
| 6,355,033 B1 | 3/2002 | Moorman et al. | |
| 6,379,349 B1 * | 4/2002 | Muller et al. | 606/41 |
| 6,464,723 B1 | 10/2002 | Callol | |
| 6,471,700 B1 | 10/2002 | Burbank et al. | |
| 6,478,793 B1 | 11/2002 | Cosman et al. | |
| 6,501,992 B1 | 12/2002 | Belden et al. | |
| 6,582,426 B2 | 6/2003 | Moorman et al. | |
| 6,622,731 B2 * | 9/2003 | Daniel et al. | 128/898 |
| 6,770,070 B1 | 8/2004 | Balbierz | |
| 6,773,446 B1 | 8/2004 | Dwyer et al. | |
| 6,893,421 B1 * | 5/2005 | Larson et al. | 604/164.01 |
| 6,902,526 B2 * | 6/2005 | Katzman | 600/104 |
| 6,966,902 B2 * | 11/2005 | Tsugita et al. | 604/509 |
| 2001/0000041 A1 * | 3/2001 | Selmon et al. | 600/585 |
| 2001/0027309 A1 | 10/2001 | Elsberry | |
| 2001/0044633 A1 * | 11/2001 | Klint | 606/200 |
| 2002/0120260 A1 | 8/2002 | Morris et al. | |
| 2002/0193781 A1 | 12/2002 | Loeb | |
| 2003/0023239 A1 | 1/2003 | Burbank et al. | |
| 2003/0032936 A1 | 2/2003 | Lederman | |
| 2003/0093007 A1 * | 5/2003 | Wood | 600/564 |
| 2003/0120195 A1 * | 6/2003 | Milo et al. | 604/19 |
| 2003/0144670 A1 * | 7/2003 | Pavcnik et al. | 606/108 |
| 2003/0158545 A1 * | 8/2003 | Hovda et al. | 606/32 |
| 2003/0212394 A1 | 11/2003 | Pearson et al. | |
| 2003/0233125 A1 * | 12/2003 | Kaplan et al. | 607/3 |
| 2004/0082942 A1 * | 4/2004 | Katzman | 606/15 |
| 2004/0106891 A1 | 6/2004 | Langan et al. | |
| 2004/0167496 A1 * | 8/2004 | Poole et al. | 604/529 |
| 2004/0187875 A1 * | 9/2004 | He et al. | 128/898 |
| 2004/0249373 A1 | 12/2004 | Gronemeyer et al. | |
| 2004/0267203 A1 | 12/2004 | Potter et al. | |
| 2005/0049570 A1 | 3/2005 | Chin et al. | |

FOREIGN PATENT DOCUMENTS

| | | | |
|---|---|---|---|
| WO | 9948548 A1 | 9/1999 | |
| WO | WO 01/45579 A1 | 12/2000 | |
| WO | WO 01/70114 A1 | 9/2001 | |

OTHER PUBLICATIONS

Lord SM, Barnsley L, Bogduk N. "Percutaneous Radiofrequency Neurotomy in the Treatment of Cervical Zygapophysial Joint Pain: A Caution", Neurosurgery 36(4):732-739, 1995.

Dreyfuss P, Rogers CJ. "Radiofrequency Neurotomy of the Zygapophyseal and Sacroiliac Joints". Pain Procedures 2:395-420, 2000.

Lau P, Mercer S, Govind J, Bogduk N. "The Surgical Anatomy of Lumbar Medial Branch Neurotomy (Facet Denervation)", Pain Medicine 5(3):289-298, 2004.

Deer T. "Injections for the Diagnosis and Treatment of Spinal Pain". American Society of Anesthesiologists 32(6):53-69, 2004.

Lord SM, Barnsley L, Wallis BJ, McDonald GJ, Bogduk N. "Percutaneous Radio-Frequency Neurotomy for Chronic Cervical Zygapopyseal-Joint Pain", New England Journal of Medicine 335(23):1721-1726, 1996.

Hooten WM, Martin DP, Huntoon MA. "Radiofrequency Neurotomy for Low Back Pain: Evidence-Based Procedural Guidelines". Pain Medicine 6(2):129-138, 2005.

Dreyfuss P, Halbrook B, Pauza K, Joshi A, McLarty J, Bogduk N. "Lumbar Radiofrequency Neurotomy for Chronic Zygapopysial Joint Pain: A Pilot Study Using Dual Medial Branch Blocks", ISIS Scientific Newsletter 3(2):13-30, 1999.

Baylis Medical Company Inc. "Technology notes—RF Lesion Size In Relation to Cannula Gauge", 2005.

Baylis Medical Company Inc. "Baylis Medical Company—Radiopaque Cannula". 2005.

Curatolo M, Reiz S. "Re: Niemisto L, Kalso E, Malmlvaara A, et al. Radiofrequency denervation for neck and back pain: a systematic review within the framework of the cochrane collabroation back review group. Spine 2003;28:1877-88", Spine 30(2):263-268, 2005.

Final Action for U.S. Appl. No. 10/382,836, "Mailed on Jan. 23, 2006".

Final Action for U.S. Appl. No. 10/382,836, "Mailed on Feb. 12, 2008".

Final Action for U.S. Appl. No. 10/382,836, "Mailed on Jun. 17, 2005".

Final Action for U.S. Appl. No. 10/382,836, "Mailed on Dec. 12, 2006".

Non-Final Action for U.S. Appl. No. 10/382,836, "Mailed on Feb. 17, 2005".

Non-Final Action for U.S. Appl. No. 10/382,836, "Mailed on Jun. 9, 2006".

Non-Final Action for U.S. Appl. No. 10/382,836, "Mailed on Jun. 19, 2007".

Non-Final Action for U.S. Appl. No. 10/382,836, "Mailed on Aug. 30, 2005".

Non-Final Action for U.S. Appl. No. 10/382,836, "Mailed on Sep. 22, 2008".

* cited by examiner

ELECTROSURGICAL DEVICE WITH IMPROVED VISIBILITY

CROSS-REFERENCE TO RELATED APPLICATIONS

This application is a continuation-in-part of U.S. patent application Ser. No. 10/382,836, filed on Mar. 7, 2003.

TECHNICAL FIELD

The invention relates to an electrosurgical device and more specifically to a device used in the treatment of pain through the application of energy.

BACKGROUND OF THE ART

Chronic back pain is a cause for concern throughout the world and especially in the United States, affecting as many as 80% of all Americans at some point in their lives. Lower back pain can arise from any number of sources, including but not limited to conditions of the spinal vertebrae themselves, the intervertebral disks and the facet joints of the spine. Although the precise cause of back pain is still a matter of debate, it is recognized that nerves present in these structures contribute to the sensation and transmission of these pain signals. Some of the recent advances in the treatment of back pain, therefore, have focused on treating the nerves deemed to be contributing to the pain sensations.

A minimally invasive technique of delivering high frequency electrical current has been shown to relieve localized pain in many patients. The high frequency electrical current is typically delivered from a generator via one or more electrodes that are placed in a patient's body. Resistance to the high frequency electrical current at the tip of the electrode causes heating of adjacent tissue and when the temperature increases sufficiently, the tissue coagulates. The temperature that is sufficient to coagulate unmyelinated nerve structures is 45° C., at which point a lesion is formed and pain signals are blocked. This procedure is known as tissue denervation and it usually results in significant pain relief. Radio frequency (RF) denervation refers to tissue denervation using energy in the RF range. This technique has proven especially beneficial in the treatment of back pain and more specifically, lower back pain.

U.S. Pat. No. 6,736,835 B2, issued May 18, 2004, U.S. Pat. No. 5,571,147, issued Nov. 5, 1996 and PCT patent application WO 01/45579 A1, published Jun. 28, 2001, amongst others, disclose methods and devices for performing RF denervation of various tissues of the back, including spinal vertebrae, intervertebral disks and facet joints of the spine. In general, the procedure entails introduction of an electrosurgical device into the body, positioning the device proximate to the neural tissue to be treated and applying RF electrical energy in order to denervate the tissue.

More specifically, an electrosurgical device comprising a cannula having a hollow shaft and a removable stylet therein is inserted into a patient's body and positioned at a desired treatment site. The cannula typically comprises an elongate, insulated region, along with an electrically conductive and exposed distal tip. Once the distal tip of the cannula is in position, the stylet is withdrawn and the distal end of a probe capable of delivering high frequency electrical energy is inserted until the distal end of the probe is at least flush with the exposed distal tip of the cannula. The proximal end of the probe is connected to a signal generator capable of generating high frequency electrical current. Once the distal end of the probe is in position, energy is supplied by the generator via the probe to denervate the tissue proximate to the distal end of the probe.

Accurate placement of the cannula requires significant technical skill and is a crucial aspect of any denervation procedure. If the cannula, and through it the probe, is positioned incorrectly, the results for the patient can be disastrous, as the denervating energy may be applied to a region of tissue that should not be denervated.

In order to facilitate accurate localization of the cannula in tissue denervation procedures, X-ray fluoroscopy is used to observe the cannula and to help guide the cannula through the body. Contrast in fluoroscopic images is achieved by means of variation in the absorbance of x-rays amongst different materials. Materials that are relatively radiopaque, such as bones and most metals, appear darker on fluoroscopic images, in contrast to the relatively radiolucent soft tissues of the body. One limitation of the technique used currently for RF denervation is that the insulated shaft of the cannula is indistinguishable from the exposed distal tip of the cannula under X-ray fluoroscopy, due to the fact that the entire cannula, i.e. both the insulated as well as the exposed regions, is generally made up of a radiopaque substance. Therefore, precise localization of the conductive distal tip of the cannula is not possible as the entire cannula, comprising both the tip and the shaft, appears dark on the fluoroscopic image. Specific localization of the distal tip of the cannula is desirable as it is this region of the cannula that is electrically exposed and is therefore responsible for creating the lesion in the tissue.

In addition to fluoroscopy, two tests are typically conducted to confirm proximity to the target nerve and to confirm that the probe is not in proximity to other nerves prior to denervation. To assess proximity to the target nerve, an electrical stimulation is applied to the probe using a frequency that excites sensory nerves, typically 50 Hz with a current of up to 1 mA. A positive stimulation result reproduces the patient's pain, without producing other sensory responses in the lower extremity or buttocks. To confirm that the probe is not in proximity to an untargeted nerve, motor nerve stimulation is performed typically at a frequency of 2 Hz and a current of 3-5 mA. In this test, a lack of elicited muscle twitch in the lower limbs confirms that the probe is not at an undesired location near a spinal nerve. In the case of negative stimulation results, where there is a failure to reproduce the patient's pain or there is clear sensory or motor stimulation of the lower extremities, denervation is not performed. Rather, the probe is repositioned and proximity testing is repeated. Providing a manner of distinguishing the conductive distal tip of the cannula in fluoroscopic images may facilitate more accurate initial placement of the distal tip and avoid the requirement for probe repositioning.

Specifically with respect to facet joint denervation, positioning the cannula at the facet joint often requires the surgeon to steer or otherwise manipulate the trajectory of the device around a neural structure known as the sympathetic chain. The sympathetic chain refers to either of the pair of ganglionated longitudinal cords of the sympathetic nervous system of which one is situated on each side of the spinal column. Due to the proximity of the sympathetic chain which carries nerves that are critical to bodily function, facet joint denervation is a specific example of a procedure that may benefit from a manner of distinguishing the cannula upon insertion in the body. The clinical success rate of this procedure ranges from 9% (Lora & Long, 1976) to 83% (Ogsbury et al., 1977). The wide range of success rates is thought to be chiefly due to variability in positioning the electrode and the resulting lesion relative to the target nerve, even when using fluoroscopy and stimulation pulses. An improvement in technique and apparatus for positioning the cannula, and through it the electrical probe, proximate to the facet nerve may increase the success rate of this procedure and eliminate improper probe positioning as a reason for poor success.

The incorporation of radiopaque markers onto surgical devices has been used in the art to increase the visibility of such devices under x-ray fluoroscopy. While techniques vary for producing and incorporating radiopaque markers onto surgical devices, the general concept involves incorporating a material with high x-ray absorption onto a specified medical device. U.S. Pat. No. 5,429,597, issued Jul. 4, 1995, discloses a balloon catheter having a radiopaque distal tip composed of a polymer mixed with a radiopaque powder such as tungsten. U.S. Pat. No. 6,315,790 B1, issued Nov. 13, 2001, describes a catheter constructed with radiopaque polymer hubs wherein the hubs accomplish the dual functions of stent crimping and radiopaque marking. Another example of a catheter with a radiopaque marker is described in U.S. Pat. No. 5,759,174, issued Jun. 2, 1998. This catheter has a single external metal marker band used to identify the central portion of the stenosis once the delivery catheter is removed.

In all of the references noted above, radiopaque markers have been applied or attached to non-radiopaque devices, such as plastic or silicone-based catheters, and not to radiopaque devices such as metallic cannulae or needles. Furthermore, due to the incorporation of a radiopaque marker, in accordance with the current state of the art, onto a device for insertion into a patient's body, the force required to insert the device into the patient's body may be significantly increased, relative to the force required to insert a device lacking such a marker. This increased force, in turn, may result in unnecessary damage to bodily tissue during insertion of such a device into a patient's body. Thus, there is a need for an electrosurgical device that overcomes some or all of the limitations of the prior art.

SUMMARY OF THE INVENTION

The present invention is directed to a cannula for insertion into a patient's body, a system for delivering energy via the cannula to a region of tissue, and a method for treating pain using the cannula.

In accordance with a first aspect of the present invention, a cannula for insertion into a patient's body is provided. The cannula optionally comprises an elongate member having a proximal end and a distal end and a lumen therebetween, and a radiopaque marker associated with the elongate member for identifying a portion of the elongate member using radiographic imaging techniques such as fluoroscopy. The radiopaque marker may be shaped to reduce the force required to insert the cannula into the patient's body, for example by having a tapered end.

As a feature of this aspect of the present invention, the elongate member is optionally electrically conductive and comprises an electrically insulated region and an electrically exposed region. In addition, the radiopaque marker is associated with at least one of the electrically insulated region and the electrically exposed region for distinguishing the exposed region from the insulated region under radiographic imaging.

According to a further aspect of the present invention, a cannula for insertion into a patient's body is provided. The cannula optionally comprises an elongate member as well as means for improving the radiographic visualization of the elongate member. Optionally, the means for improving visualization is associated with the elongate member and may be shaped in such a way so as to reduce the force required to insert the cannula into the patient's body.

As a third aspect of the present invention, a system for delivering energy to a patient's body is provided. The system comprises (i) an energy source, (ii) a cannula comprising an electrically conductive elongate member having an electrically insulated region, an electrically exposed region, and a radiopaque marker for distinguishing the insulated region from the exposed region using radiographic imaging techniques, (iii) a means of delivering energy from the energy source to the cannula, and (iv) a reference electrode. The radiopaque marker may be shaped so as to reduce the force required to insert the cannula into the patient's body, for example by being tapered at its distal end.

In accordance with a further aspect of the present invention, a method for treating pain by delivering energy to a patient's body is described. The method optionally comprises the following steps: Providing an electrically conductive cannula, comprising an electrically insulated region, an electrically exposed region and a radiopaque marker for distinguishing the insulated region from the conductive region. The electrically exposed, and thus conductive, region of the cannula is optionally positioned at a location proximate a region of tissue to be treated. The position of the electrically exposed region of the cannula is optionally determined by identifying a location of the radiopaque marker using radiographic imaging, which identification may take place at least one of before and after the step of positioning the cannula. The method optionally further comprises a step of delivering energy via the cannula to the region of tissue to be treated in order to relieve pain. The radiopaque marker may be shaped to reduce the force required to insert the cannula into the patient's body. For example, the radiopaque marker may comprise a tapered distal end.

Thus, the present invention describes a novel cannula and methods of use thereof, wherein the cannula optionally overcomes some or all of the deficiencies associated with the prior art by incorporating a radiopaque marker to allow for improved visualization of at least a portion of the cannula utilizing radiographic imaging techniques such as fluoroscopy. In addition, the radiopaque marker is optionally structured to reduce the force required to insert the cannula comprising the radiopaque marker into a patient's body.

These features and others will become apparent in the detailed description that follows.

BRIEF DESCRIPTION OF THE DRAWINGS

In order that the invention may be readily understood, embodiments of the invention are illustrated by way of examples in the accompanying drawings, in which.

DETAILED DESCRIPTION OF THE INVENTION

With specific reference now to the drawings in detail, it is stressed that the particulars shown are by way of example and for purposes of illustrative discussion of certain embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Prior to describing the drawings in detail, it should be noted that, throughout this description and corresponding drawings, like numerals are used to refer to like elements of the present invention.

Figure 1A:
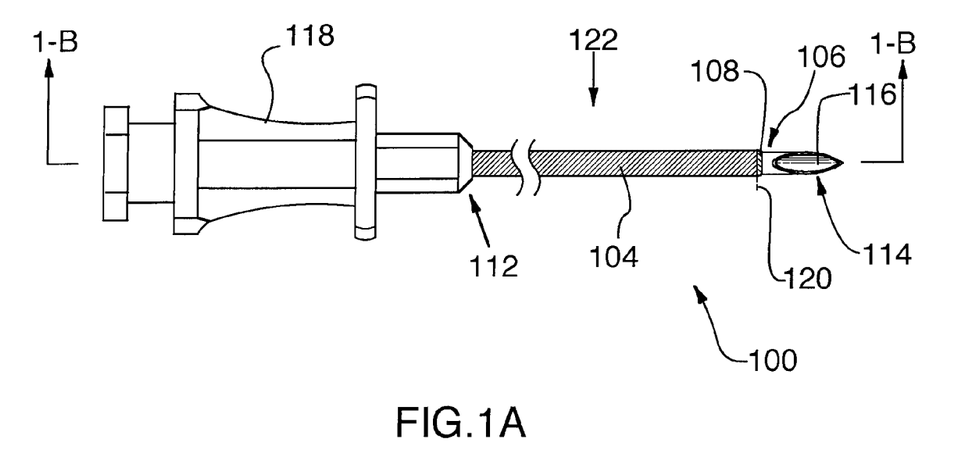
FIG. 1A is a top view of a radiopaque cannula with a radiopaque marker in accordance with the present invention.
Figure 1B:
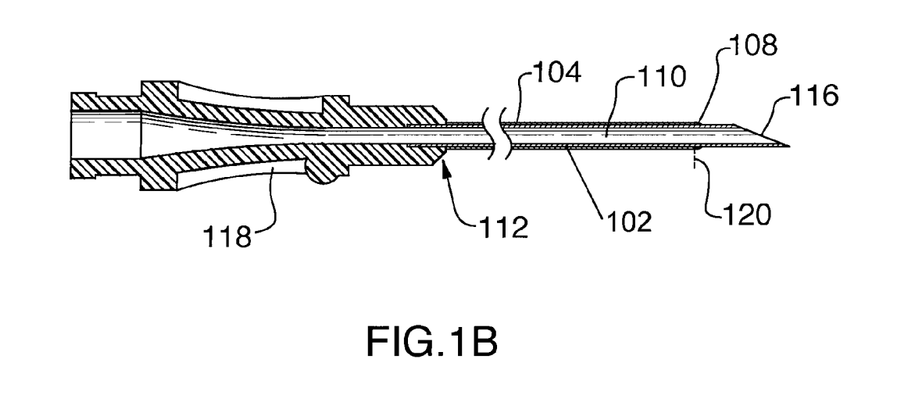
FIG. 1B is a sectional side view of the cannula depicted in FIG. 1A.

Referring first to FIGS. 1A and 1B, a first embodiment of an electrosurgical cannula 100 of the present invention is shown. FIG. 1A shows a top side view of cannula 100 while FIG. 1B illustrates a sectional view of cannula 100 along line 1B-1B in FIG. 1A. Optionally, cannula 100 is manufactured from an electrically conductive and radiopaque material, and a shaft 102 of cannula 100 is at least partially coated with an electrically insulating material 104. Suitable materials for electrically insulating material 104 include, but are not limited to, parylene and PTFE. A distal tip portion 106 of shaft 102 remains exposed and electrically conductive. Due to the conductive nature of distal tip portion 106, and for the purposes of this invention, distal tip portion 106 may be described as an active electrode or active tip. Distal tip portion 106 is optionally sharp to facilitate penetration into a patient's body. Alternatively, distal tip portion 106 may be blunt, rounded, straight, beveled, rigidly bent, or may take on other forms depending on the particular application. A radiopaque band 108, described in greater detail below, is positioned so as to distinguish active tip 106 from insulated region 122 of shaft 102 under X-ray fluoroscopic imaging.

Shaft 102 optionally defines a lumen 110 extending longitudinally from a proximal region 112 to a distal region 114 of cannula 100. In this first embodiment, distal tip portion 106 defines an aperture 116 in communication with lumen 110 of shaft 102. The combination of lumen 110 and aperture 116 allows for the introduction of a fluid or other material into a patient's body. Cannula 100 optionally further comprises a hub 118 located at or adjacent to proximal region 112. Hub 118 is optionally manufactured from ABS (Acrylonitrile Butadiene Styrene) or a similar material and may be attached to shaft 102 using various methods, including but not limited to insert molding, gluing and other forms of bonding. In the context of the present invention, the term hub indicates a fitting or any other means of facilitating a secure connection between separate components such as a cannula and a probe. As such, hub 118 is optionally structured to cooperatively engage and mate with a probe, stylet or other device which may be introduced into shaft 102. In those embodiments that comprise a hub, lumen 110 is optionally sized to simultaneously accommodate a stylet, probe or other device as well as a diagnostic or therapeutic agent. The diagnostic or therapeutic agents may include, but are not limited to, contrast or other chemical agents, pharmaceuticals, and biological agents. In other embodiments, lumen 110 may be designed to receive a probe, stylet or other device without having sufficient space to accommodate a diagnostic or therapeutic agent. In such embodiments, the probe, stylet or other device may be removed from lumen 110, allowing for injection of a diagnostic or therapeutic agent if so desired. It should be noted that, while cannula 100 has been described as having a single lumen, alternate embodiments with no lumen or more than one lumen are also envisioned. Likewise, although this embodiment depicts a cannula with a single aperture, more than one aperture may be disposed along the cannula and the one or more apertures may be disposed at various locations along cannula 100 and are not limited to the locations shown in the appended drawings.

In the first embodiment shown in FIG. 1, radiopaque band 108 is located adjacent a distal edge 120 of electrically insulating material 104, thus allowing a user to distinguish active tip 106 using radiographic imaging techniques. In other embodiments, radiopaque band 108 may be located anywhere on shaft 102 wherever improved visualization is desired. For example, radiopaque band 108 could be positioned at some location on shaft 102 along insulated region 122 and the band can be placed either on top of or under electrically insulating material 104. Covering a radiopaque marker with insulating material would be beneficial in that, compared to having an uncovered marker on the surface of a cannula, it would be easier to insert a cannula with a covered marker into a patient's body due to the fact that the insulation covering the marker would provide a more even point of contact with the patient's body, allowing for smoother insertion. Alternatively, radiopaque band 108 could be placed elsewhere on active tip 106. For example, radiopaque band 108 may be placed adjacent aperture 116 in order to determine the location and/or orientation of aperture 116. Thus, the specific location of radiopaque band 108 may vary depending on the specific requirements of the user and the invention is not limited in this regard. In addition, the radiopaque band may completely circumscribe shaft 102, as shown in the embodiment of FIG. 1, or it may only partially circumscribe shaft 102. For example, in some embodiments (not shown), the radiopaque band may only traverse 180° of the circumference of shaft 102. In such embodiments, the radiopaque band may be located on the same side of cannula 100 as the opening of aperture 116 or on the opposite side, thus allowing a user to more precisely determine the location of the opening of aperture 116.

Suitable materials for radiopaque band 108 include, but are not limited to, high-density metals such as platinum, iridium, gold, silver, tantalum or their alloys, or radiopaque polymeric compounds. Such materials are highly visible under fluoroscopic imaging and are therefore visible even at minimal thicknesses. In the embodiment depicted in FIG. 1, radiopaque band 108 has the same outer diameter as electrically insulating material 104, in order to avoid increasing the force required to insert the cannula into a patient's body.

Radiopaque band 108 is optionally laser welded to shaft 102, thus improving the heat resistance of the band-to-cannula bond and allowing the cannula to withstand multiple thermal cycles, as may be experienced when using cannula 100 in conjunction with electrosurgical procedures. In addition, the laser welding technique permits a smooth taper from shaft 102 to radiopaque band 108 as shown in FIG. 1. Radiopaque band 108 is optionally tapered at least at a distal end of radiopaque band 108, although it may additionally be tapered at a proximal end as well. Providing a radiopaque marker with a tapered distal end helps reduce the force required to insert the cannula comprising the radiopaque marker into a patient's body, due to the smooth transition, provided by the tapered marker, from an outer diameter of active tip 106 to an outer diameter of insulating material 104. In accordance with this first embodiment, the outer diameter of radiopaque band 108 is optionally substantially equivalent to the outer diameter of insulating material 104 in order to provide this smooth transition.

Alternatively, radiopaque band 108 may be applied using a number of techniques known in the art, including but not limited to vapor deposition, ion implantation, dip coating, metal plating, welding, soldering and electro plating. In addition, in embodiments wherein radiopaque band 108 is manufactured from a material such as platinum iridium, the band may be fused onto shaft 102. Radiopaque band 108 optionally has a width of 1-2 mm (approximately 0.04-0.08 inches) and more optionally 1.2-1.3 mm (approximately 0.45-0.55 inches), but this invention may be practiced with radiopaque bands of various widths and is not limited to the specific widths described in conjunction with this first embodiment.

Cannula 100 may be manufactured out of any number of suitable materials, including but not limited to stainless steel, titanium, nitinol or other radiopaque materials in order to impart varying degrees of flexibility, strength, and radiopacity to the device. Cannula 100 is optionally 18-22 AWG and 5-10 cm (approximately 2-4 inches) in length and active tip 106 is optionally 2-10 mm (approximately 0.075-0.4 inches) in length. However, cannula 100, as well as active tip 106, may be designed in a variety of gauges and lengths and the invention is not limited in this regard.

In addition to the band shown in FIGS. 1A and 1B, radiopaque markers of various shapes and patterns may be applied on selected portions of cannula 100 by, for example, the use of various masking techniques as known in the art. Selecting specific patterns of radiopacity will allow one or more of the orientation and position of cannula 100, the position of distal tip portion 106 and the position of aperture 116 to be discerned by inspection of the fluoroscopic image. FIGS. 2-5 illustrate various exemplary embodiments of patterns of radiopacity that may be adopted in accordance with this invention. It will be understood by persons skilled in the art that other shapes and patterns may be adopted as well, and the invention is not intended to be limited to the specific embodiments shown.

Figure 2:
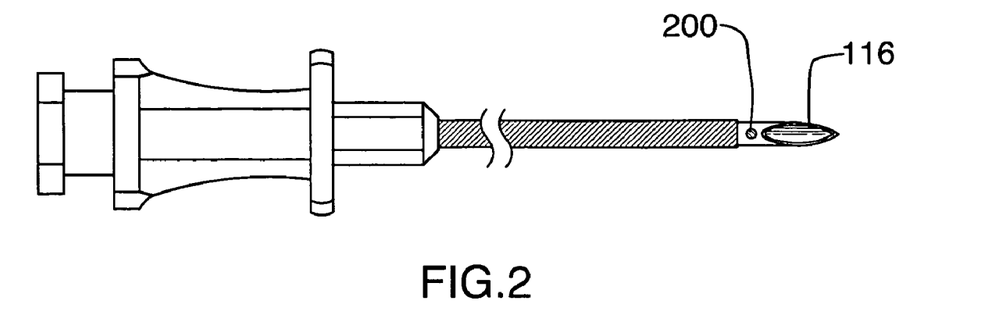
FIGS. 2 to 5 are top views illustrating alternate embodiments of a radiopaque cannula with associated radiopaque markers in accordance with the present invention.
Figure 3:
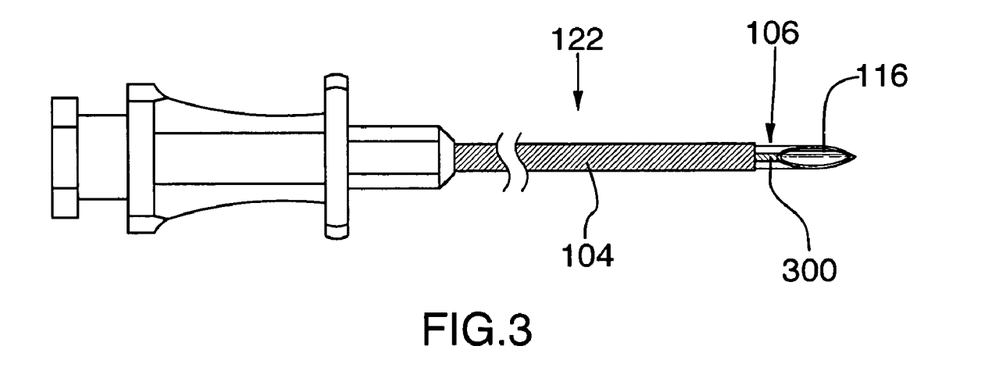

Referring now to FIG. 2, an alternate embodiment of the present invention is shown. In this embodiment, a radiopaque marker 200 may take the shape of a circle and may be placed on only one side of the shaft. As discussed above, having a radiopaque marker on only one side of the shaft may be useful in distinguishing the position and orientation of aperture 116. Similarly, the direction of a beveled tip may be identified by placing a radiopaque marker on one side of the shaft. Although FIG. 2 depicts a circular marker, it should be readily apparent to those skilled in the art that various other shapes and patterns, of various sizes, may be used and that the invention is not limited in this regard. FIG. 3 shows an alternate embodiment of the present invention, wherein a radiopaque marker 300 runs parallel to the long axis of the shaft between insulated region 122 and aperture 116 along active tip 106 thereby indicating the precise location of aperture 116 as well as the entire length of active tip 106. Variations of this embodiment may include various lengths and widths of radiopaque marker 300. For example, in some embodiments, radiopaque marker 300 may not terminate at an edge of insulated region 122 but may rather continue under or on top of insulating material 104. Alternatively, radiopaque marker 300 may not extend from aperture 116 to the edge of insulated region 122 but may rather extend from aperture 116 to another location along active tip 106.

Figure 4:
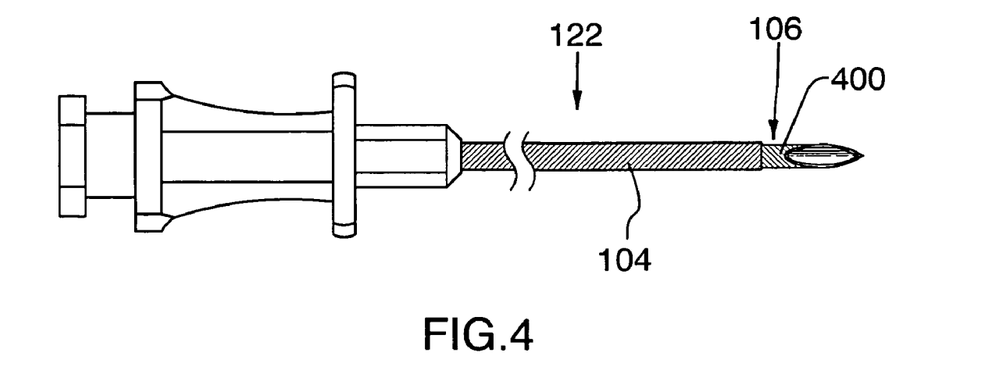
Figure 5:
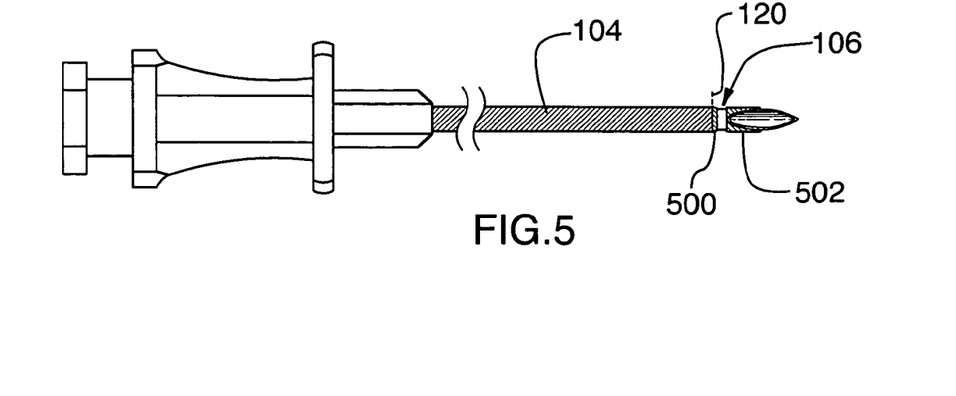

FIG. 4 illustrates yet another embodiment of the present invention wherein a radiopaque marker 400 covers the entire active tip 106 of the cannula. Such an embodiment may be manufactured by masking insulated region 122 and coating distal tip portion 106 with a suitable radiopaque material, using techniques mentioned above such as vapour deposition and ion bombardment. This embodiment would render the entire active tip 106 readily distinguishable from insulated region 122 under fluoroscopic imaging. In alternate embodiments, a section of distal tip portion 106 may be left uncoated and the invention is not limited in this regard. In an additional embodiment of a radiopaque cannula of the present invention, additionally radiopacity may be imparted to insulated region 122. For example, insulating material 104 may be rendered radiopaque using a number of techniques, including but not limited to vapour deposition, ion-bombardment and ion-implantation. Alternatively, a radiopaque marker may be applied onto a portion of shaft 102 along insulated region 122 prior to the application of insulating material 104. These embodiments would allow insulated region 122 to be distinguishable from active tip 106 under fluoroscopy due to its increased radiopacity. Referring now to the embodiment shown in FIG. 5, the cannula may comprise two radiopaque markers 500 and 502, located adjacent distal edge 120 of insulating material 104 and along a portion of distal tip portion 106, respectively. Such embodiments may be useful to distinguish various regions, for example a distal region and a proximal region, of active tip 106. The specific embodiment shown in FIG. 5 would provide a frame for active tip 106, whereby a user would have precise information regarding the entire length of active tip 106 without having to increase the radiopacity of the entire active tip region. Alternatively, the radiopaque markers may be located at any desired location of the cannula and the cannula may comprise more than two radiopaque markers.

Figure 6A:
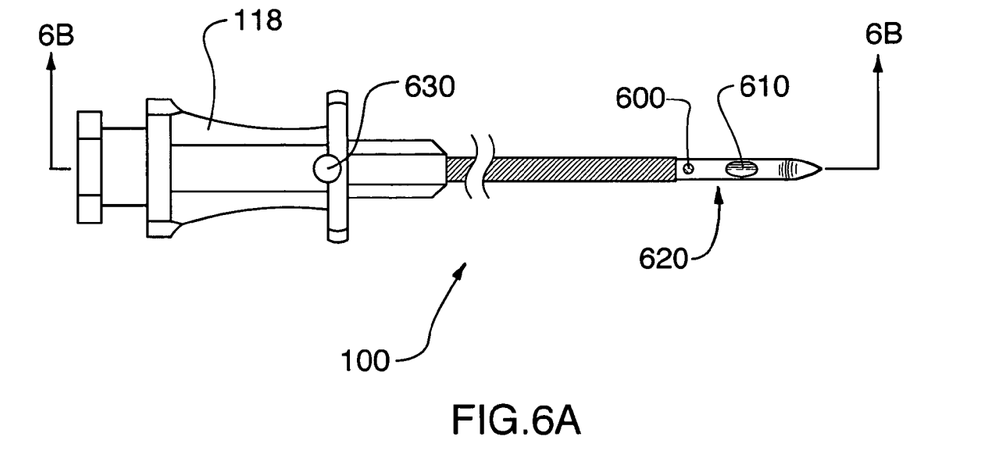
FIG. 6A is a bottom view of an embodiment of a radiopaque cannula of the present invention comprising a rigidly bent distal portion.
Figure 6B:
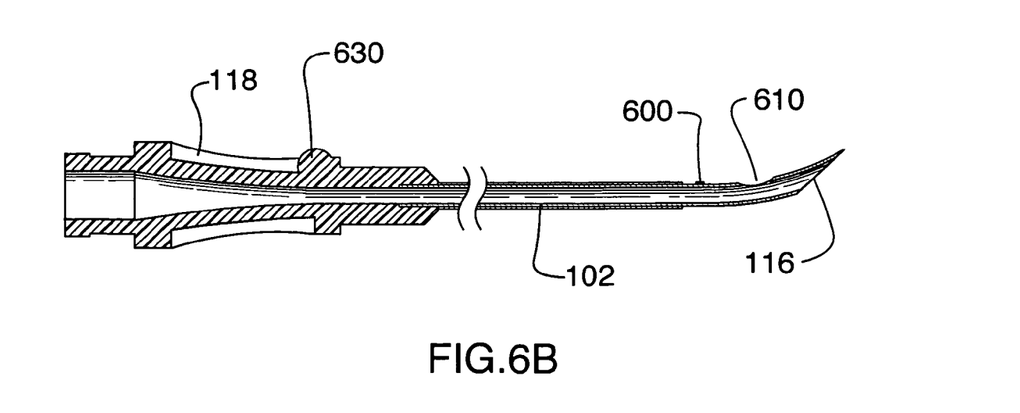
FIG. 6B is a sectional side view of the cannula depicted in FIG. 6A.

In the embodiment shown in FIGS. 6A and 6B, cannula 100 comprises a curved or rigidly bent distal tip portion 620 as well as a lateral aperture 610 which may serve as a delivery port for diagnostic or therapeutic agents. With respect to the present invention, the term 'bent' is defined to mean having a deviation from a straight line. In addition, the term 'lateral aperture' is defined as an aperture or opening defined by a lateral (or radial) surface of the cannula. This may take the form of a rigid bend or a more subtle curve, with various angles of curvature. Lateral aperture 610 induces diagnostic or therapeutic agents introduced into cannula 100 to flow along distal tip portion 620, i.e. parallel and radial to cannula 100, effectively concentrating the diagnostic or therapeutic agents in an area to be treated. Lateral aperture 610 may be disposed on any location of shaft 102, including but not limited to the inner or outer surfaces of the bend of distal tip portion 620, and additional lateral apertures may be present anywhere along the lateral surface of shaft 102. In addition, some embodiments may further comprise an aperture 116, optionally located at an end of distal tip portion 620 (as shown) to maximize delivery of the agent to the target site. Although the embodiment illustrated in FIGS. 6A and 6B shows a cannula with a single lumen, alternate embodiments may comprise a cannula with more than one lumen, whereby each lumen may be connected to one or more apertures. A radiopaque marker 600 may be located on shaft 102 in order to indicate one or more of the position and orientation of any of the lateral apertures 610 or aperture 116. The specific form and location of radiopaque marker 600 may vary and may, for example, resemble any of the aforementioned embodiments and their equivalents. This particular embodiment of the device of the present invention, comprising a lateral aperture, is especially useful for targeted delivery of anaesthetic to a nerve selected for lesioning. In addition, having a bent tip may allow for easier manoeuvrability of the cannula through a patient's body. Although the embodiment shown in FIGS. 6A and 6B comprises a bent tip, cannulae with straight tips or varying degrees of curvature may also be used in conjunction with one or more lateral apertures. In addition, hub 118 may comprise a marker 630 which may be a visual or tactile indicator to enable more accurate positioning of cannula 100. Marker 630 may be located, for example, on the same side of cannula 100 as lateral aperture 610 or on the opposite side, thus enabling a user to determine the location of lateral aperture 610 after cannula 100 has been inserted into a patient's body.

Figure 7:
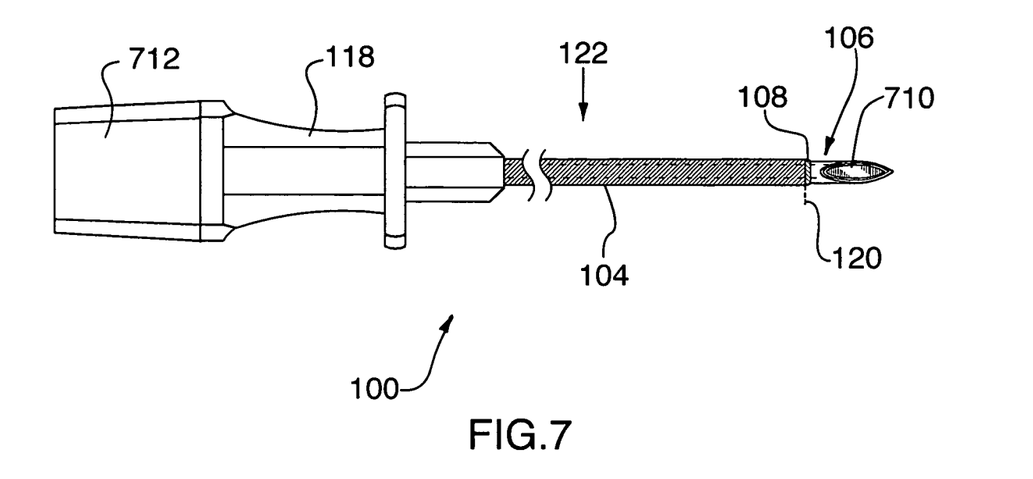
FIG. 7 is a top view of an embodiment of a radiopaque cannula of the present invention comprising a stylet.

Referring now to FIG. 7, a further embodiment of cannula 100 comprises a lumen into which a removable stylet 710 or probe (not shown) may be inserted. In this embodiment, stylet 710, shown in dotted outline, is adapted to assist in piercing a patient's skin and tissue for entry to a treatment area. As is known in the art, inserting a stylet into a cannula prior to insertion of the cannula into a patient's body helps to ensure that no tissue is forced into a lumen of the cannula by occluding any apertures in the cannula shaft. Stylet 710 optionally comprises a cap 712 adapted to cooperatively engage and mate with hub 118 of cannula 100. Optionally, stylet 710 has a pointed tip, which may be a trocar, conical, bevel, or other shape to allow for easy penetration of tissue when cannula 100 and stylet 710 are introduced into the patient's body. In the embodiment shown, and as described above with respect to FIG. 1, radiopaque band 108 is optionally located adjacent a distal edge 120 of electrically insulating material 104, thereby rendering an insulated region 122 of the shaft distinguishable from active tip 106 under fluoroscopy. However, any of the embodiments described in FIGS. 1-6 may be used in conjunction with stylet 710 and the invention is not limited in this regard.

Figure 8:
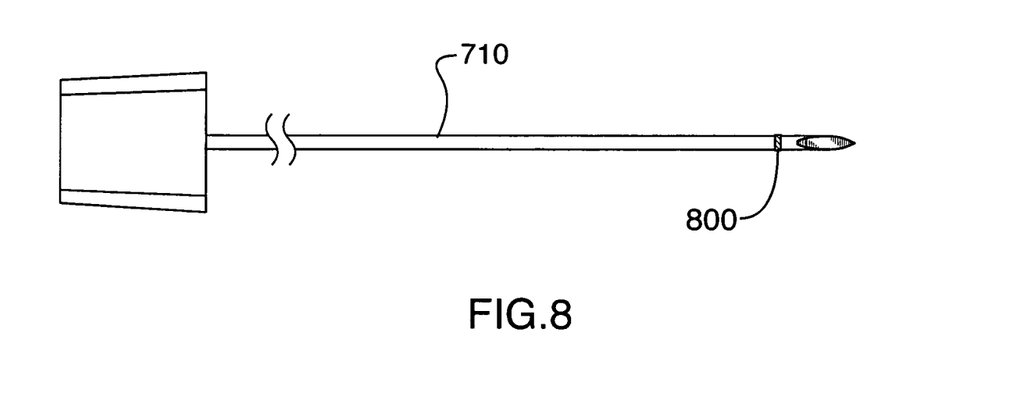
FIG. 8 is a top view of a stylet with a radiopaque marker in accordance with the present invention.

FIG. 8 shows a stylet 710 comprising a radiopaque marker 800. Radiopaque marker 800 may be located anywhere on stylet 710 and may adopt any shape and size, including but not limited to those described in the embodiments of FIGS. 1-5 and their equivalents. In the embodiment shown in FIG. 8, radiopaque marker 800 on stylet 710 may serve to identify a specific portion of the cannula shaft when stylet 710 is fully disposed within a lumen of the cannula. For example, in the embodiment shown in FIG. 8, radiopaque marker 800 may allow active tip 106 of cannula 100 (shown in FIG. 1) to be readily distinguishable from insulated region 122 under radiographic imaging when stylet 710 is fully disposed within cannula 100. It would be beneficial, in some instances, to place a radiopaque marker on the stylet rather than on the cannula itself so that this invention may be practiced with pre-existing cannulae that lack radiopaque markers without having to incorporate such radiopaque markers onto the cannulae themselves. Furthermore, incorporating a radiopaque marker onto a stylet, rather than the cannula shaft, ensures that no additional force will be required to insert the cannula into the patient's body since the stylet is located within the cannula and the cannula itself remains unchanged.

Figure 9A:
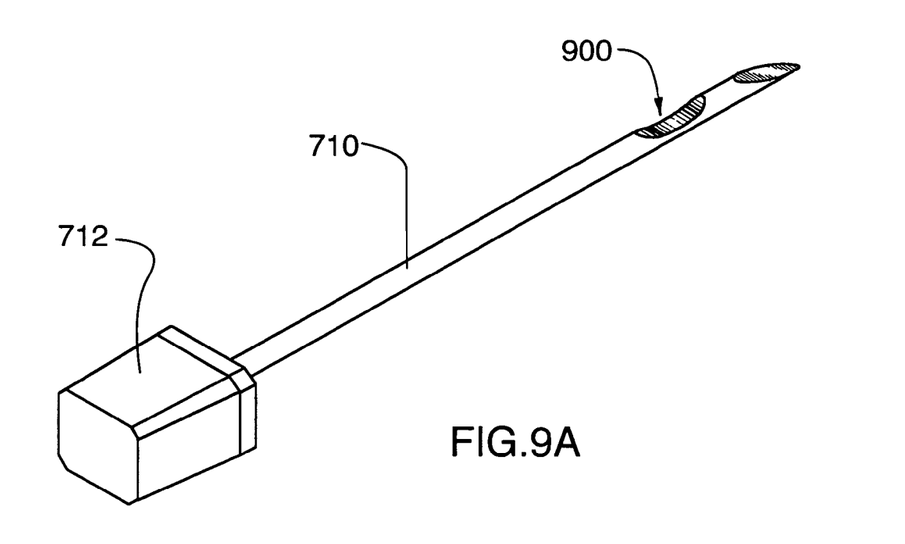
FIG. 9A is an isometric view of a stylet with a reduced mass region in accordance with the present invention.
Figure 9B:
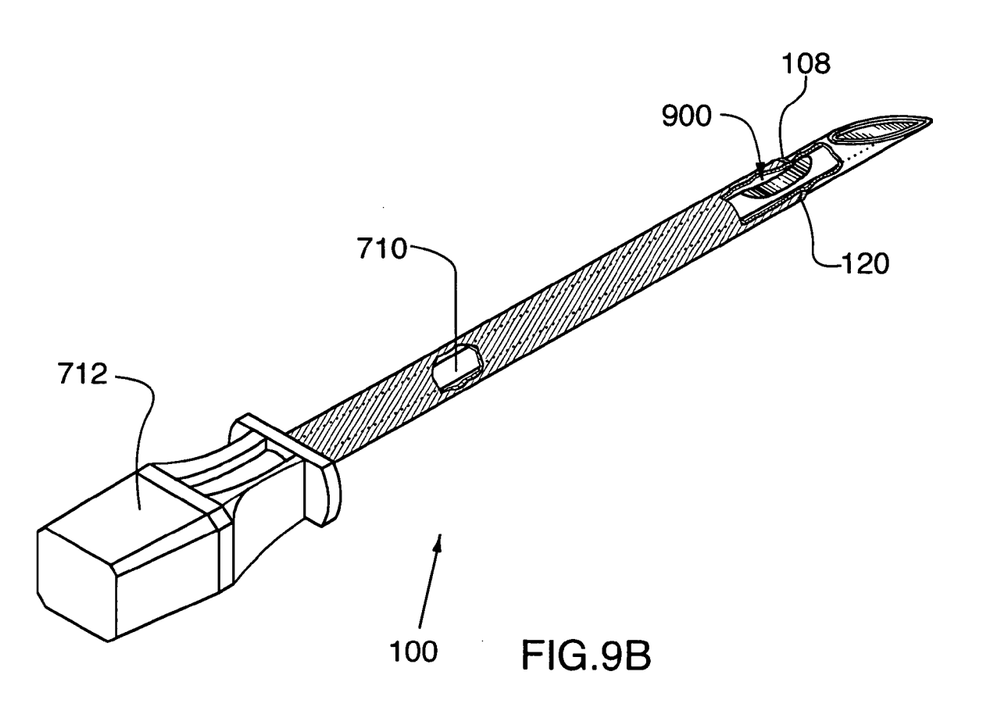
FIG. 9B is an isometric view of an embodiment of a radiopaque cannula of the present invention comprising a stylet with a reduced mass region.

Referring now to FIGS. 9A and 9B, the radiopacity of stylet 710 may be reduced at a region 900 by reducing the mass of stylet 710 at that location. The mass of stylet 710 may be reduced by removing material from stylet 710 through grinding techniques or any other means of removing material. Alternatively, stylet 710 may be originally manufactured with a reduced mass about region 900. In the embodiment shown in FIG. 9B, stylet 710 with reduced mass at region 900 could be used to improve the fluoroscopic visibility of radiopaque band 108 whereby region 900 of stylet 710 is aligned with the location of radiopaque band 108 and, due to the reduced radiopacity of region 900 (owing to the reduced mass of stylet 710 at that location), the visibility of radiopaque band 108 may be enhanced. In alternate embodiments, the cannula does not include any radiopaque markers. In such embodiments, the region of reduced mass of the stylet may be aligned with a distal edge of the insulated region of the cannula and, due to the reduced radiopacity of the stylet in this region, the distal edge of the insulated region may be more easily distinguished under fluoroscopy, thus allowing a user to determine the precise location of an active tip located adjacent the distal edge of the insulated region. In further embodiments, a radiopaque marker may be incorporated onto the stylet in conjunction with a region of reduced mass in order to allow for a thicker radiopaque marker with improved fluoroscopic visibility. In an alternative embodiment, a stylet, or a portion thereof, could be manufactured from materials of lower radiopacity than the cannula itself (for example, plastics or other non-metallic substances) in order to allow greater illumination of the radiopaque marker on the cannula under fluoroscopy. In other words, if the stylet is highly radiopaque, a radiopaque marker on the cannula will not be visible using fluoroscopy when the stylet is inserted into the cannula because the radiopacity of the stylet will mask the increased radiopacity of the radiopaque marker. Thus, if the stylet is made of a less radiopaque (or non-radiopaque) material, the radiopaque marker on the cannula may become visible even while the stylet is located within the cannula.

Figure 10:
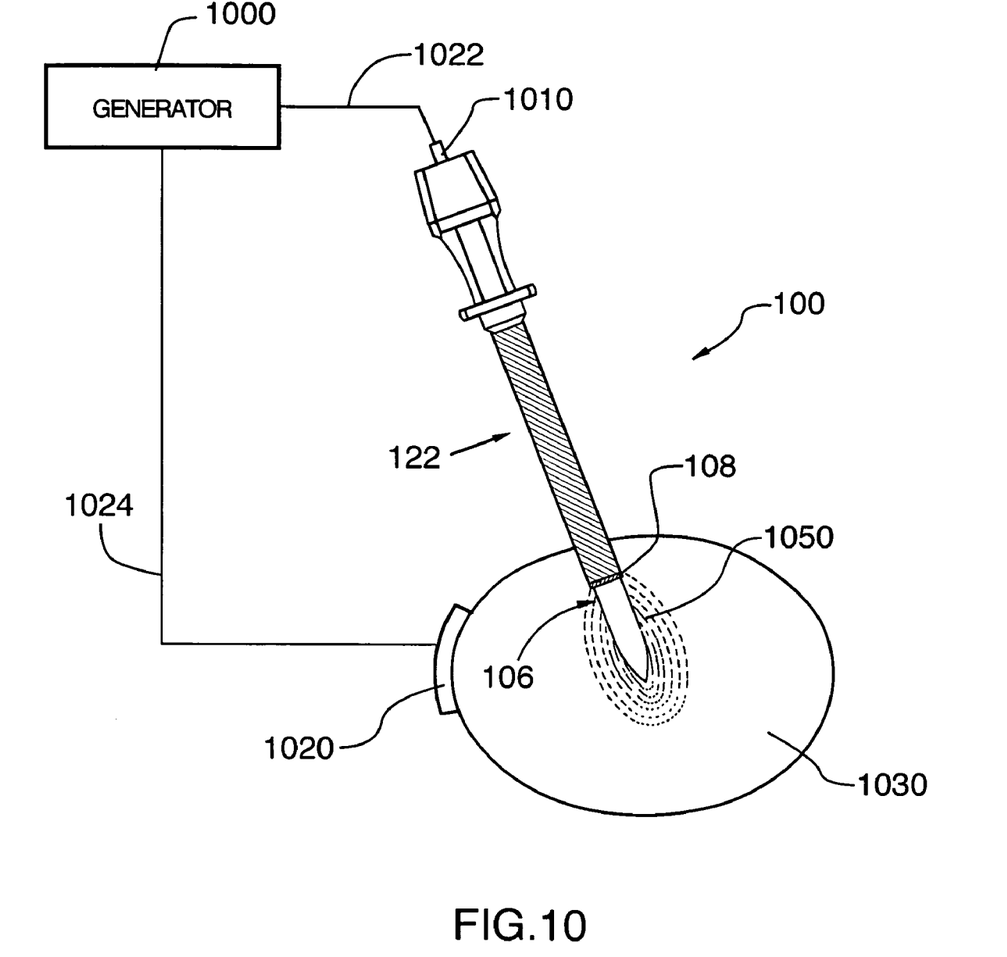
FIG. 10 is a schematic illustration of a radiopaque cannula comprising a radiopaque marker connected to a high frequency generator in accordance with the present invention.

FIG. 10 shows an electrosurgical system incorporating a device of the present invention. The electrosurgical system comprises an energy generator 1000, a cannula 100 of the present invention, a probe 1010, a reference electrode 1020 and electrical connections 1022 and 1024. In use, and as illustrated in FIG. 10, at least a portion of cannula 100 and probe 1010 are located in a region of a patient's body 1030, while reference electrode 1020 is placed at a location on the surface of body 1030. The components of the electrosurgical system of FIG. 10 will now be described in greater detail.

Energy generator 1000 may be any device capable of operating as a source of energy. In one embodiment, energy generator 1000 is an electrical generator capable of providing high-frequency electrical current. Specifically, energy generator 1000 is optionally operable in a radio-frequency (RF) range and is capable of delivering sufficient power at this frequency so as to effectively treat a patient's pain. Such treatment may take the form of an RF denervation procedure, whereby a lesion is created at a specific neural tissue through heat generated by the application of RF energy, as has been described. Other treatments are possible with such a generator, as is known in the art, and the present invention is not limited to being used in conjunction with any specific procedures.

In the embodiment shown in FIG. 10, cannula 100 comprises a radiopaque marker 108 adapted to allow a user to distinguish an electrically insulated region 122 from an active tip 106 using fluoroscopic imaging, as has been described throughout this specification. Cannula 100 is optionally structured so that an electrical connnection between probe 1010 and cannula 100 may be facilitated by the physical inter-relationship of these elements. For example, if cannula 100 is manufactured from a conductive material, physical contact between cannula 100 and probe 1010 may be sufficient to allow for a transfer of electrical energy from the probe to the cannula. In other embodiments, other means of transferring energy from probe 1010 to cannula 100 may be utilized.

Reference electrode 1020 is optionally sufficiently large to prevent localized heating on the surface of body 1030 where reference electrode 1020 is placed. In alternate embodiments, probe 1010 may contain two or more separate electrodes, whereby one electrode (the active electrode) may be electrically connected to cannula 100 and a second electrode may act as a reference electrode, replacing reference electrode 1020. In additional embodiments, reference electrode 1020 may be replaced by a reference electrode located on a second probe inserted into the body proximate to probe 1010.

Electrical connections 1022 and 1024 are any means of conveying or transmitting energy from generator 1000 to probe 1010 and from reference electrode 1020 to generator 1000. For example, electrical connections 1022 and 1024 may comprise electrical cables along with associated connectors for interfacing with generator 1000, probe 1010 and reference electrode 1020. Various other means of electrical coupling are possible and the invention is not limited in this regard.

In general, high frequency electrical current flows from generator 1000 via electrical connection 1022 to probe 1010 and via probe 1010 to active tip 106. This delivery of energy results in electrical stimulation or high frequency heating of tissue in the region surrounding active tip 106. If the tissue surrounding active tip 106 comprises one or more neural structures, the formation of a lesion 1050 may lead to pain relief due to the denervation of said neural structures.

The present invention is particularly useful for procedures where precise knowledge of the area to be treated is critical. In facet joint denervation, for example, it is critical that certain nerves, specifically those of the sympathetic chain, are not damaged during the treatment procedure. A radiofrequency treatment procedure, using a device of the present invention, may optionally be performed as follows: With a patient lying prone on a radiolucent table, a cannula of the present invention, along with a stylet disposed within a lumen of the cannula, is inserted and positioned parallel to the target nerve to be lesioned. Under fluoroscopic guidance, a radiopaque marker located on one or more of the cannula and the stylet, may assist in positioning the cannula due to the improved visualization afforded by the radiopaque marker. Once positioned, the stylet is removed and replaced by a radiofrequency probe, and the target nerve is located by sensory stimulation. At this point, the position of the active tip of the cannula may be verified using the radiopaque marker as a guide. Finally, following a test for motor stimulation as an added safety measure, energy is delivered from an energy generator through the probe to the active tip of the cannula in order to create a lesion about the target nerve. In some embodiments of the treatment procedure, anesthetic or other diagnostic or therapeutic agents may be injected through the cannula. In such embodiments, the radiopaque marker may be useful in determining the location of any apertures present on the cannula in order to effectively direct the injection of any such agents to the appropriate location. The method aspect of the present invention also provides for the insertion of multiple cannulae of the present invention over the course of a treatment procedure, whereby any or all of the cannulae may be positioned under fluoroscopic guidance, as described above.

In all of the embodiments of the present invention, cannula 100 may comprise other useful features as well as those mentioned above. For example, in some embodiments, hub 118 may comprise some type of visual or tactile marker in order to enable a user to more accurately position cannula 100 before referring to the fluoroscopic image, such as marker 630 in FIG. 6. In addition, cannula 100 may comprise one or more sensors that may be used to monitor physiological parameters such as temperature and pressure. Temperature monitoring sensors may include, but are not limited to, thermocouples, thermistors and thermometers. Pressure monitoring sensors may include, but are not limited to, pressure transducers and fluid-filled lumens in communication with fluid in a patient's body. Some embodiments of a cannula of the present invention may comprise some means of monitoring electrical impedance, in order to aid in positioning the cannula within a patient's body. In some or all of the embodiments described in this specification, distal tip portion 106 of cannula 100 may be manufactured as a separate piece and may then be attached by some means to shaft 102. Furthermore, radiopaque markers may be associated with cannula 100 at any location and the location of the radiopaque marker is not limited to the locations described in these embodiments.

It should be noted that the terms radiopaque band, marker, marking etc. as used herein denote any addition or reduction of material that increases or reduces the radiopacity of the device. Furthermore, the terms probe, cannula, stylet etc. are not intended to be limiting and denote any medical and surgical tools that can be used to perform similar functions to those described. In addition, the invention is not limited to be used in the clinical applications disclosed herein, and other medical and surgical procedures wherein a device of the present invention would be useful are included within the scope of the present invention. Furthermore, the cannulae described in the present invention are not intended to be limited to a specific length or gauge, as has been mentioned.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

We claim:

1. A radiopaque cannula for Insertion into a patient's body, the cannula comprising:
   a radiopaque and electrically conductive elongate member of a fixed length, having a proximal end and a distal end and defining a lumen therebetween, the elongate member including an electrically exposed region and an electrically Insulated region, an outer diameter of the cannula at the electrically Insulated region being larger than an outer diameter of the cannula at the electrically exposed region;
   a radiopaque marker located adjacent a distal end of the insulated region where the outer diameter of the cannula varies from the larger outer diameter of the insulated region to the smaller diameter of the exposed region, a distal end of the marker being tapered to provide a transition from the smaller outer diameter of the electrically exposed region to the larger outer diameter of the electrically insulated region; and
   the radiopaque marker being visible under radiographic imaging for distinguishing the exposed region from the insulated region.

2. The cannula of claim 1, wherein said radiopaque marker comprises a material selected from the group consisting of platinum, iridium, gold, silver, tantalum and alloys thereof.

3. The cannula of claim 1, wherein said cannula comprises material selected from the group consisting of stainless steel, titanium and nitinol.

4. The cannula of claim 1, wherein at least a portion of said distal end of said elongate member is bent.

5. The cannula of claim 1, wherein said distal end of said elongate member defines an aperture in communication with said lumen.

6. The cannula of claim 1, further comprising a lateral aperture in communication with said lumen.

7. The cannula of claim 1, further comprising at least one marker selected from the group consisting of visual markers and tactile markers.

8. The cannula of claim 1, wherein said cannula is operable to connect to an energy source.

9. The cannula of claim 1, further comprising a stylet, said stylet being insertable into said lumen.

10. The cannula of claim 9, wherein said stylet comprises a radiopaque marker.

11. The cannula of claim 1 wherein the electrically insulated region comprises a coating of an electrically insulating material disposed external to the elongate member along at least a portion of the elongate member.

12. The cannula of claim 1 wherein the marker is affixed to the elongate member by a laser weld.

13. The cannula of claim 1 wherein the radiopaque marker comprises a band that completely circumscribes the elongate member.

14. A cannula for insertion into a patient's body, said cannula comprising:
   an electrically conductive radiopaque elongate member of a fixed length, the elongate member comprising an electrically insulated region and an electrically exposed region, an outer diameter of the cannula at the insulated region being larger than an outer diameter of the cannula at the exposed region; and
   a means for improving radiographic visualization of said elongate member;
   said means for improving radiographic visualization being external to and disposed along an intermediate position of said elongate member and a distal end of said means for improving radiographic visualization being tapered to transition from the outer diameter of the cannula at the insulated region to the outer diameter of the cannula at the exposed region.

15. A system for delivering energy to a patient's body, said system comprising:
   an energy source;
   a radiopaque cannula comprising an electrically conductive radiopaque elongate member of a fixed length, the elongate member comprising an electrically insulated region, an electrically exposed region and a radiopaque marker for distinguishing the insulated region from the exposed region using radiographic imaging techniques, an outer diameter of the cannula at the insulated region being larger than an outer diameter of the cannula at the exposed region, the marker being external to and disposed along an intermediate position of the elongate member adjacent a distal end of the insulated region, and a distal end of the marker being tapered to transition from the outer diameter of the cannula at the insulated region to the outer diameter of the cannula at the exposed region;
   a means of delivering energy from said energy source to said cannula; and
   a reference electrode.

16. A method for treating pain by delivering energy to a patient's body, comprising the steps of:
   (i) providing an electrically conductive radiopaque cannula of a fixed length comprising an electrically insulated region, an electrically exposed region and a radiopaque marker located at a proximal end of the exposed region for distinguishing the insulated region from the exposed region, the marker being external to and disposed along an intermediate position of the cannula, a distal end of the marker being tapered to thereby reduce a force required to insert said cannula into said patient's body;
   (ii) identifying the radiopaque marker, distinguishing the insulated region from the exposed region and positioning the proximal end to locate said electronically exposed region proximate a region of tissue to be treated; and
   (iii) delivering energy through the cannula to said region of tissue to be treated;
   wherein the energy is delivered to relieve pain.

17. The method of claim 16, wherein the tissue to be treated is neural tissue.

18. The method of claim 17, wherein the neural tissue is located proximate to or within a facet joint of a patient's spine.

* * * * *